(12) United States Patent  (10) Patent No.: US 9,045,508 B2
Hayashi et al.  (45) Date of Patent: Jun. 2, 2015

(54) PHOSPHORUS-CONTAINING OLIGOMER AND METHOD FOR PRODUCING THE SAME, CURABLE RESIN COMPOSITION AND CURED PRODUCT OF THE SAME, AND PRINTED WIRING BOARD

(71) Applicant: DIC Corporation, Tokyo (JP)

(72) Inventors: Koji Hayashi, Ichihara (JP); Yutaka Satou, Ichihara (JP)

(73) Assignee: DIC Corporation, Tokyo (JP)

( * ) Notice: Subject to any disclaimer, the term of this patent is extended or adjusted under 35 U.S.C. 154(b) by 151 days.

(21) Appl. No.: 13/932,345

(22) Filed: Jul. 1, 2013

(65) Prior Publication Data

US 2013/0296597 A1  Nov. 7, 2013

Related U.S. Application Data

(62) Division of application No. 13/579,913, filed as application No. PCT/JP2011/051991 on Feb. 1, 2011.

(30) Foreign Application Priority Data

Feb. 18, 2010 (JP) .................................. 2010-033449

(51) Int. Cl.
*C07F 9/6574* (2006.01)
*C07F 9/30* (2006.01)
*C07F 9/6571* (2006.01)
*C08G 79/04* (2006.01)

(52) U.S. Cl.
CPC ............. *C07F 9/65746* (2013.01); *C07F 9/306* (2013.01); *C07F 9/657172* (2013.01); *C08G 79/04* (2013.01)

(58) Field of Classification Search
CPC ............... C07D 9/306; C07D 9/65746; C07D 9/657172; C08G 79/04
See application file for complete search history.

(56) References Cited

U.S. PATENT DOCUMENTS

| 8,512,466 B2 * | 8/2013 | Hayashi et al. ............... 106/310 |
| 2012/0053265 A1 | 3/2012 | Angell et al. |
| 2013/0012668 A1 | 1/2013 | Lin et al. |

FOREIGN PATENT DOCUMENTS

| JP | 2001-354685 A | 12/2001 |
| JP | 2004-143166 A | 5/2004 |

OTHER PUBLICATIONS

Ying Ling Liu, "Flame-retardant epoxy resins from novel phosphorus-containing novolac," Polymer 42, 2001 pp. 3445-3454.
Office Action dated Sep. 13, 2011, issued for the corresponding Japanese Patent Application No. 2011-532408.

* cited by examiner

*Primary Examiner* — David M Brunsman
(74) *Attorney, Agent, or Firm* — Locke Lord LLP

(57) ABSTRACT

A phosphorus-containing oligomer is represented by formula (1):

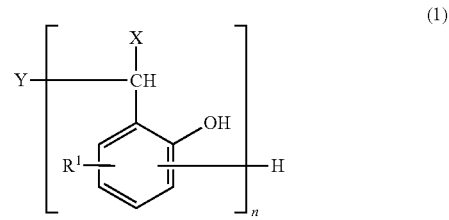

($R^1$ represents a hydrogen atom, an alkyl group having 1 to 4 carbon atoms, an alkoxy group having 1 to 4 carbon atoms, or a phenyl group; n is the number of repeating units and an integer of 1 or more; X is a structural unit represented by structural formula (x1) or (x2) below;

[Chem. 2]

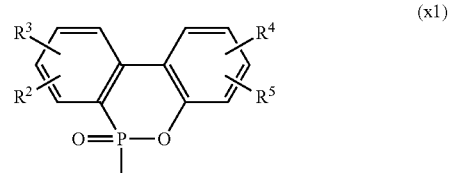

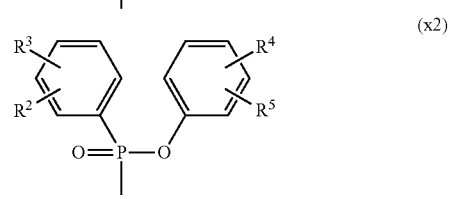

Y is a hydrogen atom, a hydroxyl group, or a structural unit represented by the formula (x1) or (x2); and, in the formula (x1) or (x2), $R^2$, $R^3$, $R^4$, and $R^5$ each independently represent a hydrogen atom, an alkyl group having 1 to 4 carbon atoms, a phenyl group, or an aralkyl group), wherein the content of components whose n is 2 or more in the formula (1) is in the range of 5% to 90% in peak area in GPC measurement.

1 Claim, 3 Drawing Sheets

US 9,045,508 B2

PHOSPHORUS-CONTAINING OLIGOMER AND METHOD FOR PRODUCING THE SAME, CURABLE RESIN COMPOSITION AND CURED PRODUCT OF THE SAME, AND PRINTED WIRING BOARD

This application is a divisional application of U.S. application Ser. No. 13/579,913, filed Aug. 17, 2012, Now U.S. Pat. No. 8,512,466, which claims the fight of priority under 35 U.S.C. §119 based on Japanese Patent Application No. 2010-033449.

TECHNICAL FIELD

The present invention relates to a phosphorus containing oligomer that has high solubility in a solvent and exhibits high flame retardancy and heat resistance in the form of a cured product thereof, a method for producing the phosphorus-containing oligomer, a curable resin composition that uses the oligomer as a curing agent for epoxy resins, a cured product of the curable resin composition, and a printed wiring board that uses the curable resin composition.

BACKGROUND ART

Epoxy resins and epoxy resin compositions containing a curing agent for epoxy resins as an essential component have excellent physical properties such as high heat resistance and moisture resistance and hence are widely used for, for example, semiconductor sealing materials, electronic components such as printed circuit boards, the electronic component field, conductive adhesives such as conductive pastes, other adhesives, matrices for composite materials, coating materials, photoresist materials, and development materials.

In recent years, further enhancement of properties such as heat resistance, moisture resistance, and solder resistance has been demanded in such various applications, in particular, applications to advanced materials. In vehicle-mounted electronic devices that are particularly required to have high reliability, the installation position has been changed from a cabin to an engine compartment having a higher temperature than a cabin. In addition, reflowing treatment temperature has increased due to use of lead-free solder. Therefore, high heat resistant materials that have higher glass transition temperature and can endure a thermal delamination test (hereinafter, abbreviated as "T288 test") have been demanded.

When epoxy resin compositions are used as materials for printed wiring boards, a flame retardant containing halogen such as bromine is added together with an antimony compound to impart flame retardancy to epoxy resin compositions. However, with efforts in terms of environment and safety in recent years, there has been a strong demand for the development of an environmentally friendly and safe method for making compositions have flame retardancy without using halogen-based flame retardants that may emit dioxins and without using antimony compounds that may cause cancer. In addition, in the field of materials for printed wiring boards, use of halogen-based flame retardants causes degradation of reliability of printed wiring boards left to stand at high temperature. Accordingly, halogen-free compositions have been highly demanded.

As for an epoxy resin composition that satisfies such required characteristics and has flame retardancy and heat resistance, for example, PTL 1 discloses a technique of using, as an epoxy resin material or a curing agent for epoxy resins, a phosphorus-containing bisphenol that is obtained as follows: 9,10-dihydro-9-oxa-10-phosphaphenanthrene-10-oxide (hereinafter, abbreviated as "HCA") is allowed to react with p-hydroxybenzaldehyde and then the reaction product is allowed to react with phenol.

However, such a phosphorus-containing bisphenol has extremely high crystallinity and exhibits almost no solubility in a solvent. Therefore, such a phosphorus-containing bisphenol cannot be prepared in the form of varnish for the printed wiring board materials, and a cured product obtained by using the phosphorus-containing bisphenol as a curing agent for epoxy resins does not have satisfactory flame retardancy. In addition, since the melting point of the phosphorus-containing bisphenol is 200° C. or more, it is extremely difficult to perform industrial production.

NPL 1 discloses a technique of producing an oligomer in THF from an intermediate product obtained through a reaction between HCA and p-hydroxybenzaldehyde.

However, in the technique disclosed in NPL 1, the reaction product of HCA and p-hydroxybenzaldehyde, which is an intermediate product, has extremely high crystallinity and thus has low solubility in a solvent. Therefore, as described in NPL 1, THF, which is a dangerous solvent having a low flash point, needs to be used in the subsequent reaction and thus it is impossible to perform industrial production. In addition, the obtained oligomer itself has low solubility in a solvent and thus it is difficult to prepare a varnish for printed wiring board materials.

Furthermore, PTL 2 discloses a technique of producing a phosphorus-containing phenolic compound through a reaction between HCA and hydroxybenzaldehyde. However, the phenolic compound disclosed in PTL 2 is a monofunctional phenolic compound and thus has extremely high crystallinity and low solubility in a solvent. In addition, even when the phenolic compound is used as a curing agent for epoxy resins, sufficient flame retardancy is not achieved.

CITATION LIST

Patent Literature

PTL 1: Japanese Unexamined Patent Application Publication No. 2004-143166
PTL 2: Japanese Unexamined Patent. Application Publication No. 2001-354685

Non Patent Literature

NPL 1: "Flame-retardant epoxy resins from novel phosphorus-containing novolac", polymer (polymer 42 (2001) 3445 to 3454), Ying Ling Liu

SUMMARY OF INVENTION

Technical Problem

Accordingly, it is an object of the present invention to provide a phosphorus-containing oligomer that has a significantly improved solubility in an organic solvent and exhibits high flame retardancy and heat resistance in the form of a cured product thereof, a method for producing the phosphorus-containing, oligomer with high industrial productivity, a curable resin composition containing the oligomer and a cured product thereof, and a printed wiring board produced from the composition.

Solution to Problem

As a result of thorough studies to address the problems above, the inventors of the present invention have found the following and have completed the present invention. That is, a phosphorus-containing oligomer obtained through a reaction between a phosphorus-containing compound such as HCA and o-hydroxybenzaldehyde exhibits high solubility in an organic solvent. Furthermore, when the oligomer is used as a curing agent for epoxy resins, an epoxy resin material, an additive for thermosetting resins, or the like and curing is performed, the cured product exhibits high flame retardancy, has high glass transition temperature, and can endure a T288 test.

The present invention relates to a phosphorus-containing oligomer represented by structural formula (1) below:

[Chem. 1]

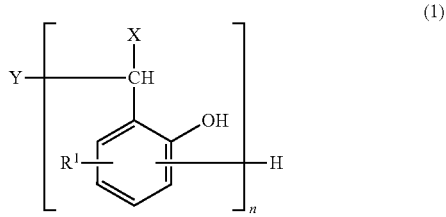

(1)

(in the formula, $R^1$ represents a hydrogen atom, an alkyl group having 1 to 4 carbon atoms, an alkoxy group having 1 to 4 carbon atoms, or a phenyl group; n is the number of repeating units and an integer of 1 or more; X is a structural unit represented by structural formula (x1) or (x2) below;

[Chem. 2]

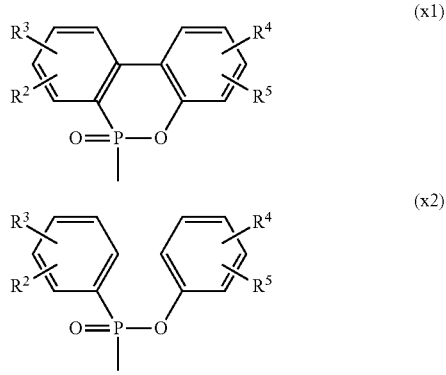

Y is a hydrogen atom, a hydroxyl group, or a structural unit represented by the structural formula (x1) or (x2); and, in the structural formula (x1) or (x2), $R^2$, $R^3$, $R^4$, and $R^5$ each independently represent a hydrogen atom, an alkyl group having 1 to 4 carbon atoms, a phenyl group, or an aralkyl group), wherein the content of components whose n is 2 or more in the structural formula (1) is in the range of 5% to 90% in terms of peak area in GPC measurement.

The present invention also relates to a method for producing a phosphorus-containing oligomer, the method including mixing a compound (a1) represented by structural formula (a1-1) or (a1-2) below and a compound (a2) represented by structural formula (a2) below with each other at a molar ratio of [compound (a1)/compound (a2)]=0.01/1.0 to 0.99/1.0; causing a reaction to proceed at 80° C. to 180° C. in the presence of an acid catalyst; then adding the compound (a1) so that the total amount on a molar basis is 1.01 to 3.0 times the amount of the compound (a2) charged; and causing a reaction to proceed at 120° C. to 200° C.,

[Chem. 3]

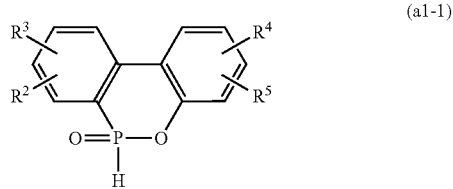

(in the formula, $R^2$, $R^3$, $R^4$, and $R^5$ each independently represent a hydrogen atom, an alkyl group having 1 to 4 carbon atoms, a phenyl group, or an aralkyl group)

[Chem. 4]

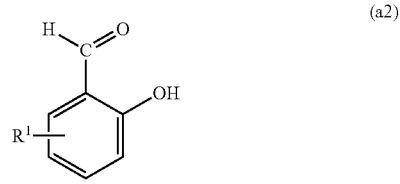

(in the formula, $R^1$ represents a hydrogen atom, an alkyl group having 1 to 4 carbon atoms, an alkoxy group having 1 to 4 carbon atoms, or a phenyl group).

The present invention also relates to a curable resin composition that includes an epoxy resin and a curing agent as essential components, wherein the phosphorus-containing oligomer is used as the curing agent.

The present invention also relates to a cured product obtained by curing the curable resin composition.

The present invention also relates to a printed wiring board obtained by further adding an organic solvent to the curable resin composition to form a resin composition in the form of varnish, impregnating a reinforcing base with the resin composition in the form of varnish, laminating a copper foil on the reinforcing base, and performing thermocompression bonding.

Advantageous Effects of Invention

According to the present invention, there can be provided a phosphorus-containing oligomer that has a significantly improved solubility in an organic solvent and exhibits high flame retardancy and heat resistance in the form of a cured product thereof, a method for producing the phosphorus-containing oligomer with high industrial productivity, a curable resin composition containing the oligomer and a cured product thereof, and a printed wiring board produced from the composition.

DESCRIPTION OF EMBODIMENTS

Figure 1:
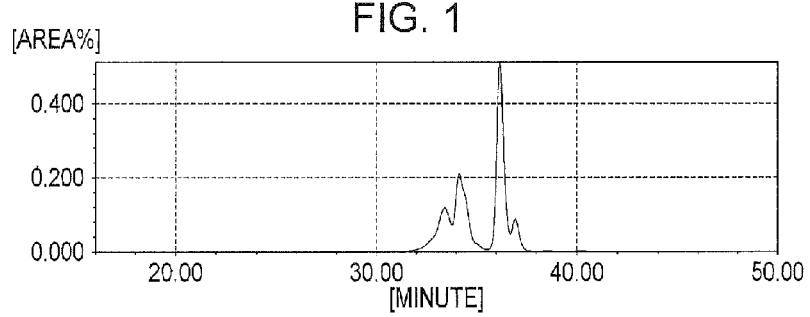
FIG. 1 shows a GPC chart of a phosphorus-containing oligomer (A-1) obtained in Example 1.

The present invention will now be described in detail.

As described above, the phosphorus-containing oligomer of the present invention is represented by structural formula (1) below:

[Chem. 5]

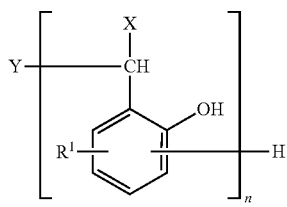
(1)

(in the formula, $R^1$ represents a hydrogen atom, an alkyl group having 1 to 4 carbon atoms, an alkoxy group having 1 to 4 carbon atoms, or a phenyl group; n is the number of repeating units and an integer of 1 or more; X is a structural unit represented by structural formula (x1) or (x2) below;

[Chem. 6]

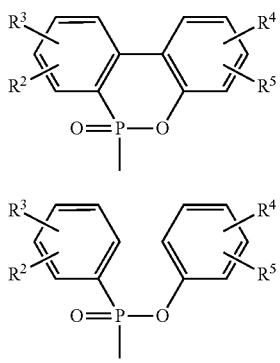

Y is a hydrogen atom, a hydroxyl group, or a structural unit represented by the structural formula (x1) or (x2); and, in the structural formula (x1) or (x2), $R^2$, $R^3$, $R^4$, and $R^5$ each independently represent a hydrogen atom, an alkyl group having 1 to 4 carbon atoms, a phenyl group, or an aralkyl group). The content of components whose n is 2 or more in the structural formula (1) is in the range of 5% to 90% in terms of peak area in GPC measurement.

The phosphorus-containing oligomer includes, as a repeating unit, a structural unit represented by structural formula (2) below in the structural formula (1):

[Chem. 7]

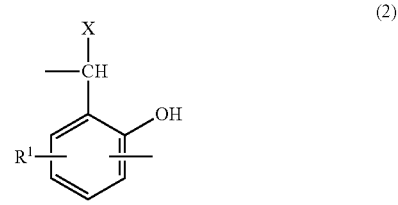
(2)

(in the formula, $R^1$ represents a hydrogen atom, an alkyl group having 1 to 4 carbon atoms, an alkoxy group having 1 to 4 carbon atoms, or a phenyl group; n is the number of repeating units and an integer of 1 or more; and X is a structural unit represented by structural formula (x1) or (x2) below).

[Chem. 8]

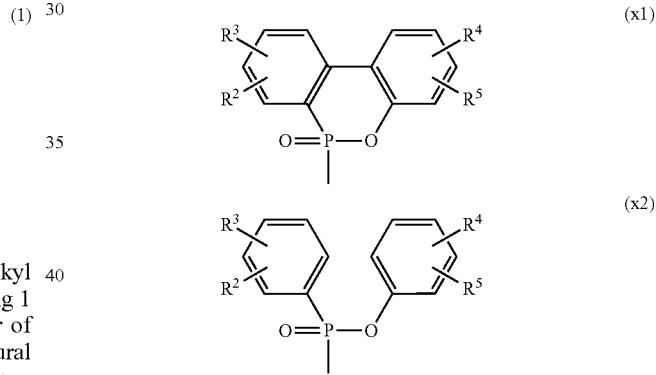

Therefore, the cured product of the phosphorus-containing oligomer has high flame retardancy, high glass transition temperature, and high thermal delamination resistance.

Specific examples of the structural unit represented by the structural formula (2) include structural units represented by structural formulae (2-1) to (2-8) below.

[Chem. 9]

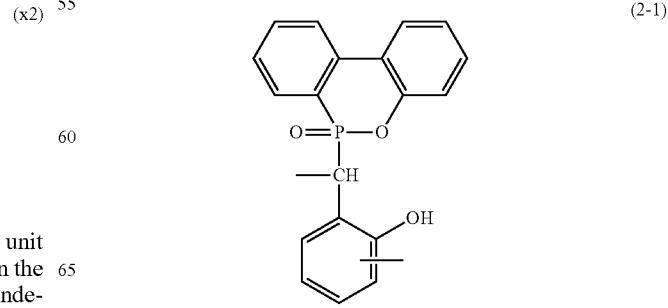
(2-1)

(2-2) 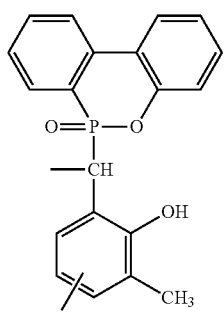

(2-3) 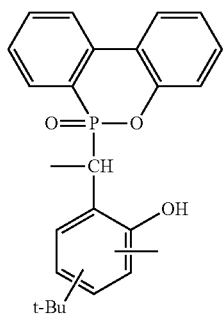

(2-4) 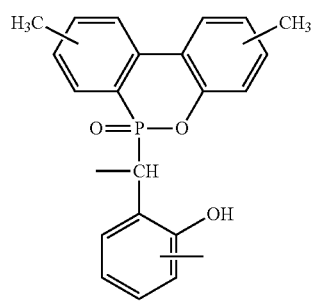

(2-5) 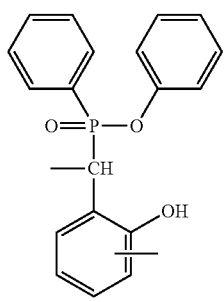

(2-6) 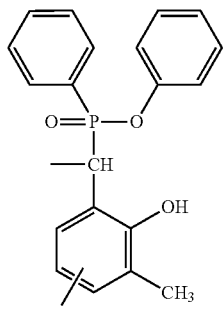

(2-7) 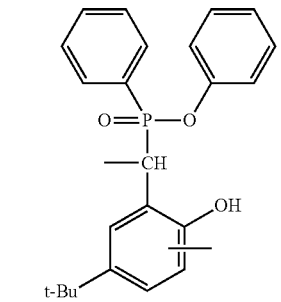

(2-8) 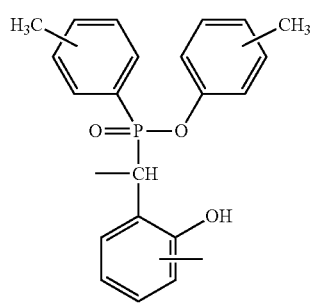

In the present invention, X in the structural formula (1) is selected from the structural units represented by the structural formulae (x1) and (x2), but is particularly preferably the structural unit represented by the structural formula (x1) in view of flame retardancy. Therefore, among the structural units represented by the structural formula (2), X is preferably selected from the structural units represented by the structural formulae (2-1), (2-2), (2-3), and (2-4) that each correspond to the structural formula (x-1).

In the structural formula (1), Y is a hydrogen atom, a hydroxyl group, or a structural unit represented by the structural formula (x1) or (x2), but they may be present together in the phosphorus-containing oligomer. In the present invention, Y is preferably a hydrogen atom or the structural unit represented by the structural formula (x1) or (x2) in view of solubility in a solvent and heat resistance and particularly preferably the structural unit represented by the structural formula (x1) in view of flame retardancy.

As described above, in the phosphorus-containing oligomer, the content of components whose n is 2 or more in the structural formula (1) is in the range of 5% to 90% in terms of peak area in GPC measurement. When the content is in the range, the solubility of the oligomer in an organic solvent and the flame retardancy of a cured product are significantly improved.

Herein, the phrase "the content of components whose n is 2 or more in the structural formula (1)" means a peak area percentage before 36.0 minutes in a GPC chart measured under the following conditions.

<GPC Measurement Conditions>
4) GPC: the measurement conditions are as follows.
Measurement apparatus: "HLC-8220 GPC" manufactured by Tosoh Corporation
Columns: guard column "HXL-L" manufactured by Tosoh Corporation,
  +"TSK-GEL G2000HXL" manufactured by Tosoh Corporation,
  +"TSK-GEL G2000HXL" manufactured by Tosoh Corporation, +"TSK-GEL G3000HXL" manufactured by Tosoh Corporation,
+"TSK-GEL G4000HXL", manufactured by Tosoh Corporation
Detector: RI (differential refractive refractometer)
Data processing: "GPC-8020 Model II version 4.10" manufactured by Tosoh Corporation
Measurement conditions: column temperature 40° C.
developing solvent tetrahydrofuran
flow rate 1.0 ml/min
Standards: the following monodisperse polystyrenes whose molecular weights are known were used in accordance with the measurement manual of the "GPC-8020 Model II version 4.10"
(Used Polystyrenes)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Samples: solutions (50 μl) obtained by filtrating a 1.0 mass % tetrahydrofuran solution in terms of resin solid matter through a micro-filter.
5) NMR: JNM-ECA500 nuclear magnetic resonance apparatus manufactured by JEOL Ltd.
Magnetic field strength: 500 MHz
Pulse width: 3.25 μsec
Number of acquisitions: 8000
Solvent: DMSO-d6
Sample concentration: 30 wt %
6) MS: AXIMA-TOF2 manufactured by SHIMADZU BIOTECH
Measurement mode: linear
Number of acquisitions: 50
Sample composition: sample/DHBA/NaTFA/THF=9.4 mg/104.7 mg/6.3 mg/1 ml In the present invention, when the content of components whose n is 2 or more is 5% or more in terms of peak area in GPC measurement, the solubility in a solvent is improved. When the content is 90% or less, the liquidity in a molten state or the liquidity in the form of varnish is improved. Herein, the other component is a component whose n is 1. Thus, in the phosphorus-containing oligomer of the present invention, the content of a component whose n is 1 is 95% to 10% in terms of peak area in GPC measurement. In the present invention, the content of components whose n is 2 or more is preferably 40% to 75% and the content of a component whose n is 1 is preferably 60% to 25% to maintain the solubility in a solvent and the fluidity and to achieve high heat resistance, in particular, to achieve high glass transition temperature and high performance in a T288 test.

More specifically, preferably, the content of a component whose n is 1 is 95% to 10%, the content of a component whose n is 2 is 3% to 50%, and the content of components whose n is 3 or more is 1% to 45% in view of solubility in a solvent. Particularly preferably, the content of a component whose n is 1 is 60% to 25%, the content of a component whose n is 2 is 10% to 45%, and the content of components whose n is 3 or more is 10% to 40% in view of good balance of solubility in a solvent, liquidity, and heat resistance.

As described above, Y in the structural formula (1) is preferably a structural unit represented by the structural formula (x1). Therefore, a phosphorus-containing oligomer in which, in the structural formula (1), Y is a structural unit represented by the structural formula (x1), the content of components whose n is 2 or more is 40% to 75%, and the content of a component whose n is 1 is 60% to 25% is preferably employed in view of flame retardancy and heat resistance. A phosphorus-containing oligomer in which, in the structural formula (1), Y is a structural unit represented by the structural formula (x1), the content of a component whose n is 1 is 95% to 10%, the content of a component whose n is 2 is 3% to 50%, and the content of components whose n is 3 or more is 1% to 45% is more preferably employed in view of high flame retardancy, heat resistance, and solubility in a solvent. A phosphorus-containing oligomer in which Y is a structural unit represented by the structural formula (x1), the content of a component whose n is 1 is 60% to 25%, the content of a component whose n is 2 is 10% to 45%, and the content of components whose n is 3 or more is 10% to 40% is most preferably employed in view of good balance of flame retardancy, solubility in a solvent, liquidity, and heat resistance.

In the phosphorus-containing oligomer, the content of phosphorus in the oligomer is preferably 9% to 12% by mass in view of flame retardancy. The content of phosphorus is measured in conformity with "JIS K0102 46".

The phosphorus-containing oligomer described in detail is preferably a phosphorus-containing oligomer produced by the following production method of the present invention to achieve high solubility in an organic solvent and high heat resistance of a cured product.

As described above, the production method of the present invention includes mixing a compound (a1) represented by structural formula (a1-1) or (a1-2) below and a compound (a2) represented by structural formula (a2) below with each other at a molar ratio of [compound (a1)/compound (a2)]=0.01/1.0 to 0.99/1.0; causing a reaction to proceed at 80° C. to 180° C. in the presence of an acid catalyst; then adding the compound (a1) so that the total amount on a molar basis is 1.01 to 3.0 times the amount of the compound (a2) charged; and causing a reaction to proceed at 120° C. to 200° C.

[Chem. 10]

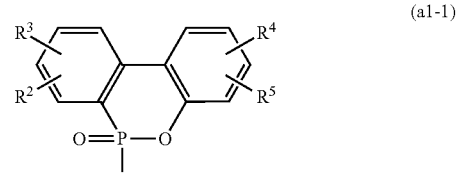

(a1-1)

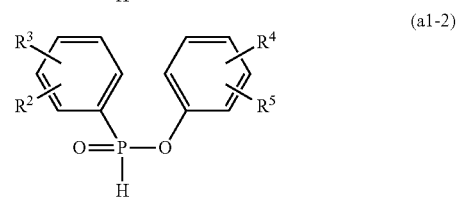

(a1-2)

(In the formula, $R^2$, $R^3$, $R^4$, and $R^5$ each independently represent a hydrogen atom, an alkyl group having 1 to 4 carbon atoms, a phenyl group, or an aralkyl group.)

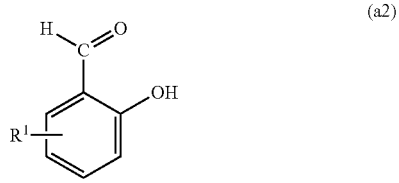

(a2)

(In the formula, $R^1$ represents a hydrogen atom, an alkyl group having 1 to 4 carbon atoms, an alkoxy group having 1 to 4 carbon atoms, or a phenyl group)

In the present invention, when a phosphorus-containing oligomer is produced by the method above, the precipitation of a reaction intermediate can be favorably reduced and higher molecular weight is easily achieved.

Examples of the alkyl group having 1 to 5 carbon atoms that constitutes $R^2$, $R^3$, $R^4$, and $R^5$ in the structural formula (a1-1) or (a1-2) include a methyl group, an ethyl group, an n-propyl group, an i-propyl group, and a t-butyl group. However, in the compound (a1) used in the present invention, $R^2$, $R^3$, $R^4$, and $R^5$ are each preferably a hydrogen atom in view of flame retardancy. Furthermore, the compound (a1) is preferably represented by the structural formula (a1-1) in view of high flame retardancy of a cured product. In the compound (a2), examples of $R^1$ in the structural formula (a2) include a methyl group, an ethyl group, an n-propyl group, and a methoxy group, but $R^1$ is preferably a hydrogen atom in view of the reactivity with the compound (a1) and high flame retardancy of a cured product.

Examples of the catalyst that can be used in the method include inorganic acids such as hydrochloric acid, sulfuric acid, and phosphoric acid; organic acids such as methanesulfonic acid, p-toluenesulfonic acid, and oxalic acid; and Lewis acids such as boron trifluoride, anhydrous aluminum chloride, and zinc chloride. The amount of such a catalyst used is preferably 0.1% to 5.0% by mass relative to the total weight of charged raw materials in order to prevent a decrease in electrical insulation of a cured product.

Since the compound (a2) is liquid, the reaction can be caused to proceed using the compound (a2) as an organic solvent. However, other organic solvents may be used to improve the work efficiency or the like. The organic solvent may be a non-ketonic organic solvent such as an alcohol organic solvent or a hydrocarbon organic solvent. Specifically, the alcohol organic solvent may be propylene glycol monomethyl ether and the hydrocarbon organic solvent may be toluene or xylene.

After the reaction, an intended product can be obtained by performing drying under reduced pressure.

The curable resin composition of the present invention is a curable resin composition including an epoxy resin and a curing agent as essential components, and the phosphorus-containing oligomer of the present invention is used as the curing agent.

The epoxy resin used herein may be various epoxy resins. Examples of the epoxy resin include bisphenol epoxy resins such as a bisphenol A epoxy resin and a bisphenol F epoxy resin; biphenyl epoxy resins such as a biphenyl epoxy resin and a tetramethyl biphenyl epoxy resin; novolac epoxy resins such as a phenolic novolac epoxy resin, a cresol novolac epoxy resin, a bisphenol A novolac epoxy resin, epoxidized condensates derived from a phenol and an aromatic aldehyde having a phenolic hydroxyl group, and a biphenyl novolac epoxy resin; triphenylmethane epoxy resins; tetraphenylethane epoxy resins; dicyclopentadiene-phenol addition reaction epoxy resins; phenol aralkyl epoxy resins; epoxy resins intramolecularly having a naphthalene skeleton, such as a naphthol novolac epoxy resin, a naphthol aralkyl epoxy resin, a naphthol-phenol cocondensation novolac epoxy resin, a naphthol-cresol cocondensation novolac epoxy resin, diglycidyloxynaphthalene, and 1,1-bis(2,7-diglycidyloxy-1-naphthyl)alkane; and phosphorus-containing epoxy resins. These epoxy resins may be used alone or in combination of two or more thereof.

Examples of the phosphorus-containing epoxy resin include epoxidized products of a phenolic resin obtained through a reaction between 9,10-dihydro-9-oxa-10-phosphaphenanthrene-10-oxide (hereinafter, abbreviated as "HCA") and a quinone, epoxy resins obtained by modifying a phenolic novolac epoxy resin with HCA, epoxy resins obtained by modifying a cresol novolac epoxy resin with HCA, epoxy resins obtained by modifying a bisphenol A epoxy resin with a phenolic resin obtained through a reaction between HCA and a quinone, and epoxy resins obtained by modifying a bisphenol F epoxy resin with a phenolic resin obtained through a reaction between HCA and a quinone.

Among the above-described epoxy resins, novolac epoxy resins and epoxy resins having a naphthalene skeleton in the molecular structure are particularly preferred in view of heat resistance; and bisphenol epoxy resins and novolac epoxy resins are preferred in view of solubility in a solvent.

The amounts of the epoxy resin and the phosphorus-containing oligomer in the curable resin composition of the present invention are not particularly limited. The amounts are preferably set such that the amount of active hydrogen in the phosphorus-containing oligomer is 0.7 to 1.5 equivalents per equivalent of epoxy groups in total of the epoxy resin because a cured product to be obtained has good characteristics.

In the curable resin composition of the present invention, a curing agent other than the phosphorus-containing oligomer may be used as the curing agent for epoxy resins so long as the advantages of the present invention are not impaired. Such another curing agent may be an amine compound, an amide compound, an acid anhydride compound, a phenolic compound, or the like. Specific examples of the amine compound include diaminodiphenylmethane, diethylenetriamine, triethylenetetramine, diaminodiphenyl sulfone, isophoronediamine, imidazole, $BF_3$-amine complexes, and guanidine derivatives. Specific examples of the amide compound include dicyandiamide and polyamide resins synthesized from a dimer of linolenic acid and ethylenediamine. Specific examples of the acid anhydride compound include phthalic anhydride, trimellitic anhydride, pyromellitic dianhydride, maleic anhydride, tetrahydrophthalic anhydride, methyltetrahydrophthalic anhydride, methylnadic anhydride, hexahydrophthalic anhydride, and methylhexahydrophthalic anhydride. Specific examples of the phenolic compound include polyhydric phenolic compounds such as a phenolic novolac resin, a cresol novolac resin, an aromatic hydrocarbon formaldehyde resin-modified phenolic resin, a dicyclopentadiene-phenol adduct resin, a phenol aralkyl resin (Xylok resin), naphthol aralkyl resin, a trisphenylolmethane resin, a tetraphenylolethane resin, a naphthol novolac resin, a naphthol-phenol cocondensation novolac resin, a naphthol-cresol cocondensation novolac resin, a biphenyl-modified phenolic resin (a polyhydric phenolic compound in which phenolic nuclei are bonded to each other through bismethylene groups), a biphenyl-modified naphthol resin (a polyhydric naphthol compound in which phenolic nuclei are bonded to each other through bismethylene groups), an aminotriazine-modified phenolic resin (a compound intramolecularly having a phenolic skeleton, a triazine ring, and a primary amino group), and an alkoxy-group-containing aromatic ring modified novolac resin (a polyhydric phenolic compound in which phenolic nuclei and alkoxy-group-containing aromatic rings are bonded to each other through formaldehyde).

Among these compounds, compounds intramolecularly having a large number of aromatic skeletons are particularly preferred in view of excellent low thermal expansion of a cured product. Specifically, in view of excellent low thermal expansion, preferred examples of the compounds include a phenolic novolac resin, a cresol novolac resin, an aromatic hydrocarbon formaldehyde resin-modified phenolic resin, a phenol aralkyl resin, a naphthol aralkyl resin, a naphthol novolac resin, a naphthol-phenol cocondensation novolac resin, a naphthol-cresol cocondensation novolac resin, a biphenyl-modified phenolic resin, a biphenyl-modified naphthol resin, an aminotriazine-modified phenolic resin, and an alkoxy-group-containing aromatic ring modified novolac resin (a polyhydric phenolic compound in which phenolic nuclei and alkoxy-group-containing aromatic rings are bonded to each other through formaldehyde).

As for the aminotriazine-modified phenolic resin, that is, a compound intramolecularly having a phenolic skeleton, a triazine ring, and a primary amino group, a compound having a molecular structure obtained by condensation reaction between a triazine compound, a phenol, and an aldehyde is preferred because a cured product has high flame retardancy.

In view of the flame retardancy of a cured product, the other curing agent described above is preferably used such that the content of phosphorus in the solid matter of the curable resin composition according to the present invention is 1% to 9%.

If necessary, the curable resin composition of the present invention may also appropriately contain a curing accelerator. Various curing accelerators can be used as the curing accelerator. Examples of the curing accelerator include phosphorus compounds, tertiary amines, imidazole, metal salts of organic acids, Lewis acids, and amine complex salts. In particular, when the curable resin composition is used as a semiconductor sealing material, a preferred phosphorus compound is triphenyl phosphine and a preferred amine compound is 2-ethyl-4-methylimidazole in view of excellent curing properties, heat resistance, electric characteristics, moisture resistance reliability, and the like. The amount of the curing accelerator used is preferably 0.01% to 1% by mass in the curable resin composition.

As described above, the curable resin composition of the present invention having been described so far in detail exhibits high solubility in a solvent. Therefore, the curable resin composition preferably contains, in addition to the above-described components, an organic solvent. Examples of the organic solvent that can be used include methyl ethyl ketone, acetone, dimethylformamide, methyl isobutyl ketone, methoxy propanol, cyclohexanone, methyl cellosolve, ethyl diglycol acetate, and propylene glycol monomethyl ether acetate. The selection of the solvent and the appropriate amount of the solvent used can be appropriately determined on the basis of the application. For example, in applications to printed wiring boards, alcohol organic solvents or carbonyl group-containing organic solvents having a boiling point of 160° C. or less, such as methyl ethyl ketone, acetone, and 1-methoxy-2-propanol are preferred and such organic solvents are preferably used such that a nonvolatile content is 40% to 80% by mass. In applications to adhesive films for build-up, the organic solvent is preferably a ketone such as acetone, methyl ethyl ketone, or cyclohexanone; an acetate such as ethyl acetate, butyl acetate, cellosolve acetate, propylene glycol monomethyl ether acetate, or carbitol acetate; a carbitol such as cellosolve or butyl carbitol; an aromatic hydrocarbon such as toluene or xylene; or dimethylformamide, dimethylacetamide, N-methylpyrrolidone, or the like. In addition, the organic solvent is preferably used such that a nonvolatile content is 30% to 60% by mass.

To achieve flame retardancy, the curable resin composition may contain a non-halogen flame retardant that substantially contains no halogen atoms in the field of, for example, printed wiring boards as long as reliability is not degraded.

Examples of the non-halogen flame retardant include phosphorus flame retardants, nitrogen flame retardants, silicone flame retardants, inorganic flame retardants, and organic metal salt flame retardants. Use of these flame retardants is not limited at all. The flame retardants may be used alone, in combination of flame retardants of the same type, or in combination of flame retardants of different types.

Inorganic and organic flame retardants can be used as the phosphorus flame retardants. Examples of such inorganic compounds include red phosphorus and inorganic nitrogen-containing phosphorus compounds such as ammonium phosphates (e.g., monoammonium phosphate, diammonium phosphate, triammonium phosphate, and ammonium polyphosphate) and phosphoric acid amide.

The red phosphorus is preferably surface-treated in order to prevent hydrolysis and the like. Examples of such a surface treatment method include (i) a method of forming a coating with an inorganic compound such as magnesium hydroxide, aluminum hydroxide, zinc hydroxide, titanium hydroxide, bismuth oxide, bismuth hydroxide, bismuth nitrate, or a mixture of the foregoing; (ii) a method of forming a coating with a mixture of an inorganic compound such as magnesium hydroxide, aluminum hydroxide, zinc hydroxide, or titanium hydroxide, and a thermosetting resin such as a phenolic resin; and (iii) a method of forming a coating with a thermosetting resin such as a phenolic resin on a coating made of an inorganic compound such as magnesium hydroxide, aluminum hydroxide, zinc hydroxide, or titanium hydroxide to provide double coatings.

Examples of the organic phosphorus compounds include, in addition to general-purpose organic phosphorus compounds such as phosphoric acid ester compounds, phosphonic acid compounds, phosphinic acid compounds, phosphine oxide compounds, phosphorane compounds, and organic nitrogen-containing phosphorus compounds, cyclic organic phosphorus compounds such as 9,10-dihydro-9-oxa-10-phosphaphenanthrene=10-oxide, 10-(2,5-dihydroxyphenyl)-10H-9-oxa-10-phosphaphenanthrene=10-oxide, and 10-(2,7-dihydroxynaphthyl)-10H-9-oxa-10-phosphaphenanthrene=10-oxide, and derivatives obtained by reactions between the cyclic organic phosphorus compounds and compounds such as epoxy resins and phenolic resins.

The amount of a phosphorus flame retardant added is appropriately selected on the basis of the type of the phosphorus flame retardant, other components in the curable resin composition, and a desired degree of flame retardancy. For example, in 100 parts by mass of a curable resin composition containing all components such as an epoxy resin, a curing agent, a non-halogen flame retardant, a filler, and other additives, when red phosphorus is used as a non-halogen flame retardant, red phosphorus is preferably added in the range of 0.1 to 2.0 parts by mass. Similarly, when an organic phosphorus compound is used, the organic phosphorus compound is preferably added in the range of 0.1 to 10.0 parts by mass, particularly preferably, in the range of 0.5 to 6.0 parts by mass.

When the phosphorus flame retardant is used, the phosphorus flame retardant may be used together with hydrotalcite, magnesium hydroxide, boride compounds, zirconium oxide, black dyes, calcium carbonate, zeolite, zinc molybdate, activated carbon, or the like.

Examples of the nitrogen flame retardants include triazine compounds, cyanuric acid compounds, isocyanuric acid compounds, and phenothiazine. Triazine compounds, cyanuric acid compounds, and isocyanuric acid compounds are preferred.

Examples of the triazine compounds include melamine, acetoguanamine, benzoguanamine, melon, melam, succinoguanamine, ethylenedimelamine, melamine polyphosphate, and triguanamine; aminotriazine sulfate compounds such as guanylmelamine sulfate, melem sulfate, and melam sulfate; the above-described aminotriazine-modified phenolic resin; and compounds obtained by further modifying the aminotriazine-modified phenolic resin with tung oil, isomerized linseed oil, or the like.

Specific examples of the cyanuric acid compounds include cyanuric acid and melamine cyanurate.

The amount of such a nitrogen flame retardant added is appropriately selected on the basis of the type of the nitrogen flame retardant, other components in the curable resin composition, and a desired degree of flame retardancy. For example, in 100 parts by mass of a curable resin composition containing all components such as an epoxy resin, a curing agent, a non-halogen flame retardant, a filler, and other additives, the nitrogen flame retardant is preferably added in the range of 0.05 to 10 parts by mass, particularly preferably, in the range of 0.1 to 5 parts by mass.

Such a nitrogen flame retardant may be used together with a metal hydroxide, a molybdenum compound, or the like.

The silicone flame retardants are not particularly limited as long as the silicone flame retardants are organic compounds having silicon atoms. Examples of the silicone flame retardants include silicone oil, silicone rubber, and silicone resin.

The amount of such a silicone flame retardant added is appropriately selected on the basis of the type of the silicone flame retardant, other components in the curable resin composition, and a desired degree of flame retardancy. For example, in 100 parts by mass of a curable resin composition containing all components such as an epoxy resin, a curing agent, a non-halogen flame retardant, a filler, and other additives, the silicone flame retardant is preferably added in the range of 0.05 to 20 parts by mass. Such a silicone flame retardant may be used together with a molybdenum compound, alumina, or the like.

Examples of the inorganic flame retardants include metal hydroxides, metal oxides, metal carbonate compounds, metal powders, boron compounds, and low-melting glass.

Specific examples of the metal hydroxides include aluminum hydroxide, magnesium hydroxide, dolomite, hydrotalcite, calcium hydroxide, barium hydroxide, and zirconium hydroxide.

Specific examples of the metal oxides include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Specific examples of the metal carbonate compounds include zinc carbonate, magnesium carbonate, calcium carbonate, barium carbonate, basic magnesium carbonate, aluminum carbonate, iron carbonate, cobalt carbonate, and titanium carbonate.

Specific examples of the metal powders include powders of aluminum, iron, titanium, manganese, zinc, molybdenum, cobalt, bismuth, chromium, nickel, copper, tungsten, and tin.

Specific examples of the boron compounds include zinc borate, zinc metaborate, barium metaborate, boric acid, and borax.

Specific examples of the low-melting glass include CEEPREE (Bokusui Brown Co., Ltd.), hydrated glass $SiO_2$—MgO—$H_2O$, and glassy compounds of PbO—$B_2O_3$, ZnO—$P_2O_5$—MgO, $P_2O_5$—$B_2O_3$—PbO—MgO, P—Sn—O—F, PbO—$V_2O_5$—$TeO_2$, $Al_2O_3$—$H_2O$, and lead borosilicate.

The amount of such an inorganic flame retardant added is appropriately selected on the basis of the type of the inorganic flame retardant, other components in the curable resin composition, and a desired degree of flame retardancy. For example, in 100 parts by mass of a curable resin composition containing all components such as an epoxy resin, a curing agent, a non-halogen flame retardant, a filler, and other additives, the inorganic flame retardant is preferably added in the range of 0.05 to 20 parts by mass, particularly preferably, in the range of 0.5 to 15 parts by mass.

Examples of the organic metal salt flame retardants include ferrocene, acetylacetonato metal complexes, organic metal carbonyl compounds, organic cobalt salt compounds, organic metal sulfonates, and compounds in which metal atoms and aromatic compounds or heterocyclic compounds are bonded to each other through ionic bonds or coordinate bonds.

The amount of such an organic metal salt flame retardant added is appropriately selected on the basis of the type of the organic metal salt flame retardant, other components in the curable resin composition, and a desired degree of flame retardancy. For example, in 100 parts by mass of a curable resin composition containing all components such as an epoxy resin, a curing agent, a non-halogen flame retardant, a filler, and other additives; the organic metal salt flame retardant is preferably added in the range of 0.005 to 10 parts by mass.

The curable resin composition of the present invention may optionally contain an inorganic filler. Examples of the inorganic filler include fused silica, crystalline silica, alumina, silicon nitride, and aluminum hydroxide. When the amount of such an inorganic filler added is made particularly large, fused silica is preferably used. The fused silica may be used in the form of fragments or spheres. To increase the amount of fused silica added and to suppress an increase in the melt viscosity of the composition, fused silica in the form of spheres is preferably mainly used. To increase the amount of spherical silica added, the size distribution of silica particles is preferably appropriately adjusted. The filling factor of the filler is preferably high in view of flame retardancy and particularly preferably 20% by mass or more relative to the whole amount of the curable resin composition. In applications to conductive paste and the like, a conductive filler such as silver powder or copper powder may be used.

The curable resin composition of the present invention may optionally contain various additives such as a silane coupling agent, a release agent, a pigment, and an emulsifying agent.

The curable resin composition of the present invention can be obtained by uniformly mixing the components above. The curable resin composition can be easily cured by a method similar to known methods. Examples of such a cured product include formed cured products such as multilayer products, cast products, adhesive layers, coatings, and films.

Examples of applications of the curable resin composition according to the present invention include printed wiring board materials, resin compositions for flexible wiring boards, interlayer insulating materials for build-up boards, semiconductor sealing materials, conductive pastes, adhesive films for build-up, resin casting materials, and adhesives.

Among these various applications, in the applications to insulating materials for printed wiring boards and electronic circuit boards and adhesive films for build-up, the curable resin composition can be used as insulating materials for boards within which passive components such as capacitors and active components such as IC chips are embedded, so-called electronic-component built-in boards.

Among these, the curable resin composition has characteristics of high flame retardancy, high heat resistance, and solubility in a solvent and hence is preferably used for printed wiring board materials, resin compositions for flexible wiring boards, and interlayer insulating materials for build-up boards. The curable resin composition is particularly preferably used for printed circuit boards.

A printed circuit board of the present invention can be produced from the curable resin composition of the present invention by a method in which a curable resin composition that is in the form of varnish and contains an epoxy resin, a phosphorus-containing oligomer, and furthermore an organic solvent is impregnated into a reinforcing base; a copper foil is laminated on the reinforcing base; and the resultant laminate is subjected to thermocompression bonding. Examples of the reinforcing base that can be used herein include paper, glass cloth, glass nonwoven fabric, aramid paper, aramid cloth, glass mat, and glass roving cloth. Such a method will be further described in detail. The curable resin composition in the form of varnish is heated to a heating temperature according to the type of a solvent used, preferably to 50° C. to 170° C., to provide a prepreg that is a cured product. The mass ratio of the resin composition and the reinforcing base that are used herein is not particularly limited, but the mass ratio is generally preferably adjusted such that the resin content in the prepreg is 20% to 60% by mass. The thus-obtained prepreg is then stacked by a standard method, a copper foil is appropriately laminated thereon, and the resultant laminate is subjected to thermocompression bonding under a pressure of 1 to 10 MPa at 170° C. to 250° C. for 10 minutes to 3 hours, whereby an intended printed circuit board can be provided.

A flexible wiring board is produced from the curable resin composition of the present invention as follows. The phosphorus-containing oligomer, an epoxy resin, and an organic solvent and optionally another curing agent and a curing accelerator are mixed with each other and applied onto an electrical insulating film with a coater such as a reverse roll coater or a comma coater. The electrical insulating film is then heated with a heater at 60° C. to 170° C. for 1 to 15 minutes to evaporate the solvent, whereby the adhesive composition is brought into the B-stage. A metal foil is then bonded to the adhesive by thermocompression bonding with a heating roll or the like. At this time, the compression bonding pressure is preferably 2 to 200 N/cm and the compression bonding temperature is preferably 40° C. to 200° C. When sufficient bonding properties are achieved at this time, this procedure may be finished. When complete curing is required, postcure is preferably further performed at 100° C. to 200° C. for 1 to 24 hours. The adhesive composition film finally cured preferably has a thickness in the range of 5 to 100 µm.

An interlayer insulating material for build-up boards is produced from the curable resin composition of the present invention by, for example, the following method. The curable resin composition appropriately containing rubber, a filler, and the like is applied onto a wiring board in which circuits have been formed by a spray coating method, a curtain coating method, or the like and is subsequently cured. Holes are then optionally made in predetermined through-hole portions and the like. The board is treated with a roughening agent and the surface thereof is rinsed with hot water to form irregularities. The board is plated with a metal such as copper. The plating method is preferably electroless plating or electrolytic plating. Examples of the roughening agent include an oxidizing agent, an alkali, and an organic solvent. Such a procedure is sequentially repeated as needed to alternately build up a resin insulating layer and a conductor layer having a predetermined circuit pattern. As a result, a build-up board can be provided. Note that holes are made in the through-hole portions after the formation of a resin insulating layer serving as an outermost layer. Alternatively, a build-up board can be produced without the plating process as follows: a copper foil with a resin in which the resin composition has been semi-cured on the copper foil is bonded to a wiring board in which circuits have been formed by thermocompression bonding at 170° C. to 250° C., whereby a roughened surface is formed.

An adhesive film for build-up is produced from the curable resin composition of the present invention by, for example, a method in which the curable resin composition of the present invention is applied onto a support film to form a resin composition layer, whereby an adhesive film for multilayer printed wiring boards is provided.

When the curable resin composition of the present invention is used for an adhesive film for build-up, it is important that the adhesive film softens under a lamination temperature condition (generally 70° C. to 140° C.) in a vacuum lamination method and exhibits liquidity (resin flow) with which via holes or through-holes in a circuit board can be filled with the resin at the same time as lamination of the circuit board. The above-described components are preferably mixed with each other so that such characteristics are exhibited.

Herein, through-holes in multilayer printed wiring boards generally have a diameter of 0.1 to 0.5 mm and a depth of 0.1 to 1.2 mm, and it is preferable that through-holes satisfying these ranges can be filled with the resin. Note that, when lamination is performed on both surfaces of a circuit board, through-holes are desirably filled to about half of the through-holes.

Specifically, the above-described method for producing an adhesive film can be performed as follows. The curable resin composition in the form of varnish according to the present invention is prepared. The varnish composition is then applied onto a surface of a support film and the organic solvent is subsequently removed by heating, hot-air blowing, or the like to form a layer ($\alpha$) of the curable resin composition.

The formed layer ($\alpha$) generally has a thickness equal to or larger than the thickness of a conductor layer. Since a circuit board generally has a conductor layer with a thickness in the range of 5 to 70 µm, the resin composition layer preferably has a thickness of 10 to 100 µm.

Note that the layer ($\alpha$) may be covered with a protective film described below. By protecting the surface of the resin composition layer with a protective film, adhesion of dust or the like to the surface and scratching formed on the surface can be prevented.

The support film and the protective film may be composed of, for example, a polyolefin such as polyethylene, polypropylene, or polyvinyl chloride; a polyester such as polyethylene terephthalate (hereinafter, sometimes abbreviated as "PET") or polyethylene naphthalate; polycarbonate; polyimide; release paper; or a metal foil such as copper foil or aluminum foil. Note that the support film and the protective film may be subjected to a mat treatment, a corona treatment, and a release treatment.

The thickness of the support film is not particularly limited and is generally 10 to 150 μm and preferably 25 to 50 μm. The thickness of the protective film is preferably 1 to 40 μm.

The above-described support film is detached after the lamination is performed on a circuit board or after an insulating layer is formed by heat-curing. By detaching the support film after the adhesion film is heat-cured, adhesion of dust or the like in the curing step can be prevented. When the support film is detached after the curing, the support film is generally subjected to a release treatment in advance.

A method for producing a multilayer printed wiring board with the thus-obtained adhesive film is performed by, for example, in the case where the layer (α) is protected with a protective film, removing the protective film and performing lamination such that the layer (α) is in direct contact with a single surface or both surfaces of a circuit board by, for example, a vacuum lamination method. The lamination may be performed by a batch process or a continuous process with rolls. The adhesive film and the circuit board may be optionally heated (preheated) before the lamination.

As for the lamination conditions, lamination is preferably performed at a compression bonding temperature (lamination temperature) of 70° C. to 140° C., at a compression bonding pressure of 1 to 11 kgf/cm$^2$ ($9.8 \times 10^4$ to $107.9 \times 10^4$ N/m$^2$), and under a reduced air pressure of 20 mmHg (26.7 hPa) or less.

When the curable resin composition of the present invention is used as a conductive paste, for example, there are a method in which fine conductive particles are dispersed in the curable resin composition to provide a composition for an anisotropic conductive film and a method in which the curable resin composition is turned into a resin composition paste for circuit connection or an anisotropic conductive adhesive, the resin composition paste and the anisotropic conductive adhesive being in a liquid state at room temperature.

In the preparation of a semiconductor sealing material from the curable resin composition of the present invention, an epoxy resin composition prepared for semiconductor sealing materials can be produced by sufficiently melt-mixing the epoxy resin, the phosphorus-containing oligomer, the curing accelerator, and optionally another epoxy resin curing agent, and additives such as an inorganic filler optionally using an extruder, a kneader, a roll, or the like until uniform mixing is achieved. At this time, the inorganic filler is generally silica. The filling factor of the inorganic filler is preferably in the range of 30% to 95% by mass relative to 100 parts by mass of the epoxy resin composition; particularly preferably 70 parts by mass or more to improve flame retardancy, moisture resistance, and resistance to solder cracking and to decrease linear expansion coefficient; and more preferably 80 parts by mass or more to considerably improve the advantages. As for semiconductor package forming, there is a method in which the composition is formed by casting or with a transfer molding apparatus, an injection molding apparatus, or the like and then heated at 50° C. to 200° C. for 2 to 10 hours to provide formed products serving as semiconductor devices.

The method for providing the cured product of the present invention may be performed in conformity with a typical method for curing a curable resin composition. For example, the heating temperature may be appropriately selected in accordance with the types of curing agents combined or the applications. In general, the composition obtained by the above method may be heated at about 20° C. to 250° C.

Accordingly, by using the phosphorus-containing oligomer, the solubility in a solvent is considerably improved compared with existing phosphorus-modified phenolic resins; and, in the form of a cured product, flame retardancy, heat resistance, and heat resistance reliability can be exhibited and applications to the most advanced printed wiring board materials can be achieved. In addition, the phenolic resin can be efficiently and readily produced by the production method of the present invention and molecular design according to the degree of the intended properties can be performed.

EXAMPLES

The present invention will now be specifically described based on Examples and Comparative Examples. Note that melt viscosity at 180° C., softening point, the content of phosphorus, GPC measurement, NMR, and MS spectrum were measured under the following conditions.
1) Melt viscosity at 180° C.: conformity with ASTM D4287
2) Softening-point measurement method: JIS K7234
3) Method for measuring the content of phosphorus: conformity with JIS K0102-46
4) GPC: the measurement conditions are as follows.
   Measurement apparatus: "HLC-8220 GPC" manufactured by Tosoh Corporation
   Columns: guard column "HXL-L" manufactured by Tosoh Corporation,
   +"TSK-GEL G2000HXL" manufactured by Tosoh Corporation,
   +"TSK-GEL G2000HXL" manufactured by Tosoh Corporation,
   +"TSK-GEL G3000HXL" manufactured by Tosoh Corporation,
   +"TSK-GEL G4000HXL", manufactured by Tosoh Corporation
Detector: RI (differential refractive refractometer)
Data processing: "GPC-8020 Model II version 4.10" manufactured by Tosoh Corporation
Measurement conditions: column temperature 40° C.
   developing solvent tetrahydrofuran
   flow rate 1.0 ml/min
Standards: the following monodisperse polystyrenes whose molecular weights are known were used in accordance with the measurement manual of the "GPC-8020 Model II version 4.10"
   (Used Polystyrenes)
   "A-500" manufactured by Tosoh Corporation
   "A-1000" manufactured by Tosoh Corporation
   "A-2500" manufactured by Tosoh Corporation
   "A-5000" manufactured by Tosoh Corporation
   "F-1" manufactured by Tosoh Corporation
   "F-2" manufactured by Tosoh Corporation
   "F-4" manufactured by Tosoh Corporation
   "F-10" manufactured by Tosoh Corporation
   "F-20" manufactured by Tosoh Corporation
   "F-40" manufactured by Tosoh Corporation
   "F-80" manufactured by Tosoh Corporation
   "F-128" manufactured by Tosoh Corporation
Samples: solutions (50 μl) obtained by filtrating a 1.0 mass % tetrahydrofuran solution in terms of resin solid matter through a micro-filter.
5) NMR: JNM-ECA500 nuclear magnetic resonance apparatus manufactured by JEOL Ltd.
Magnetic field strength: 500 MHz
Pulse width: 3.25 μsec
Number of acquisitions: 8000
Solvent: DMSO-d6
Sample concentration: 30 mass %

6) MS: AXIMA-TOF2 manufactured by SHIMADZU BIOTECH
Measurement mode: linear
Number of acquisitions: 50
Sample composition: sample/DHBA/NaTFA/THF=9.4 mg/104.7 mg/6.3 mg/1 ml The content of components whose number of repeating units in the structural formula (1) is 2 or more (hereinafter abbreviated as n=2 or more) was calculated based on a peak area before 36.0 minutes in a GPC chart.

Example 1

Synthesis of Phosphorus-Containing Oligomer (A-1)

A flask equipped with a thermometer, a cooling tube, a fractional distillation column, a nitrogen-gas inlet tube, and a stirrer was charged with 122 g (1.0 mol) of 2-hydroxybenzaldehyde, 151.2 g (0.7 mol) of 9,10-dihydro-9-oxa-10-phosphaphenanthrene-10-oxide (hereinafter, abbreviated as "HCA"), and 2.23 g (0.019 mol) of oxalic acid. The mixture was heated to 120° C. to allow the reaction to proceed for one hour. Subsequently, 172.8 g (0.8 mol) of HCA was added to the flask, and the mixture was heated to 180° C. to allow the reaction to proceed for three hours. Water was then removed under heating and reduced pressure to obtain 410 g of a phosphorus-containing oligomer (A-1) having a structural unit represented by structural formula below.

[Chem. 12]

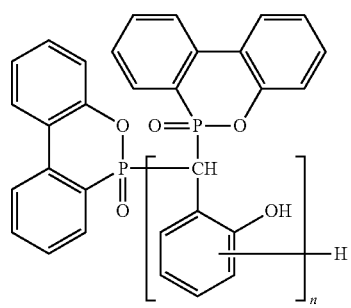

Figure 2:
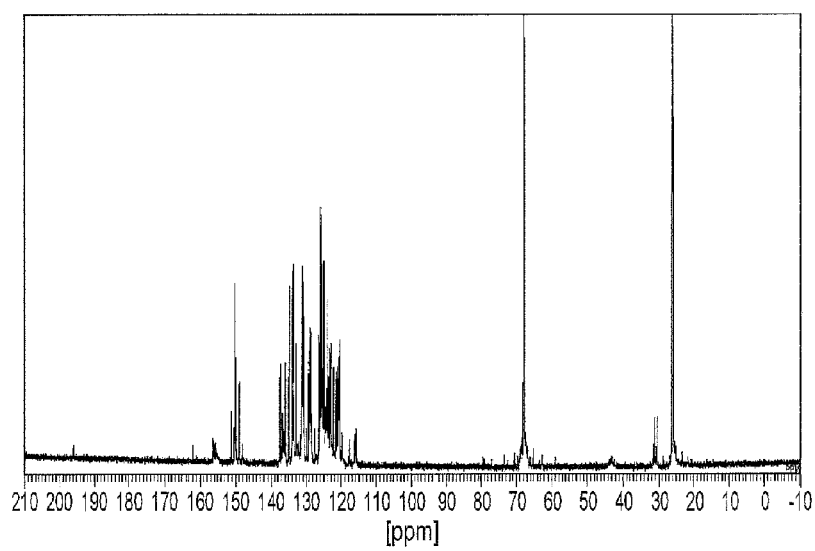
FIG. 2 shows a $^{13}$C-NMR chart of the phosphorus-containing oligomer (A-1) obtained in Example 1.
Figure 3:
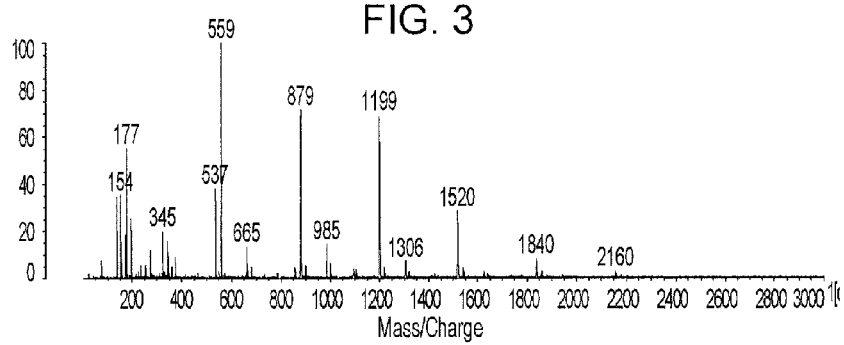
FIG. 3 shows an MS spectrum of the phosphorus-containing oligomer (A-1) obtained in Example 1.

The obtained phosphorus-containing oligomer had a softening point of 138° C. (B&R method), a melt viscosity (measurement method: ICI viscometer method, measurement temperature: 180° C.) of 66 dPa·s, a hydroxyl equivalent of 428 g/eq, and a phosphorus content of 10.5%. The content of a component whose n=1 was 51%, the content of a component whose n=2 was 29.6%, and the content of components whose n=3 or more was 19.4% (the content of components whose n=2 or more was 49.0%). FIG. 1 shows a GPC chart of the obtained phosphorus-containing oligomer. FIG. 2 shows a $^{13}$C-NMR chart of the obtained phosphorus-containing oligomer. FIG. 3 shows an MS spectrum of the obtained phosphorus-containing oligomer.

Example 2

Synthesis of Phosphorus-Containing Oligomer (A-2)

A flask equipped with a thermometer, a cooling tube, fractional distillation column, a nitrogen-gas inlet tube, and a stirrer was charged with 122 g (1.0 mol) of o-hydroxybenzaldehyde, 108 g (0.5 mol) of HCA, and 2.23 g (0.019 mol) of oxalic acid. The mixture was heated to 120° C. to allow the reaction to proceed for one hour. Subsequently, 216 g (1.0 mol) of HCA was added to the flask, and the mixture was heated to 180° C. to allow the reaction to proceed for three hours. Water was then removed under heating and reduced pressure to obtain 415 g of a phosphorus-containing oligomer (A-2) having a structural unit represented by structural formula below.

[Chem. 13]

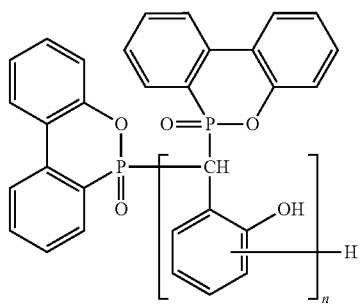

Figure 4:
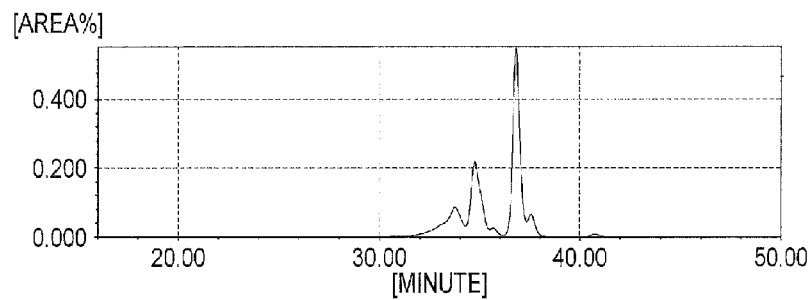
FIG. 4 shows a GPC chart of a phosphorus-containing oligomer (A-2) obtained in Example 2.

The obtained phosphorus-containing oligomer had a softening point of 130° C. (B&R method), a melt viscosity (measurement method: ICI viscometer method, measurement temperature: 180° C.) of 72 dPa·s, a hydroxyl equivalent of 430 g/eq, and a phosphorus content of 10.5 mass %. The content of a component whose n=1 was 55.3%, the content of a component whose n=2 was 26.0%, and the content of components whose n=3 or more was 18.7% (the content of components whose n=2 or more was 44.7%). FIG. 4 shows a GPC chart of the obtained phenolic resin.

Example 3

Synthesis of Phosphorus-Containing Oligomer (A-3)

A flask equipped with a thermometer, a cooling tube, a fractional distillation column, a nitrogen-gas inlet tube, and a stirrer was charged with 122 g (1.0 mol) of o-hydroxybenzaldehyde, 129.6 g (0.6 mol) of HCA, and 3.81 g (0.032 mol) of oxalic acid. The mixture was heated to 120° C. to allow the reaction to proceed for one hour. Subsequently, 129.6 g (0.6 mol) of HCA was added to the flask, and the mixture was heated to 180° C. to allow the reaction to proceed for three hours. Water was then removed under heating and reduced pressure to obtain 415 g of a phosphorus-containing oligomer (A-3) having a structural unit represented by structural formula below.

[Chem. 14]

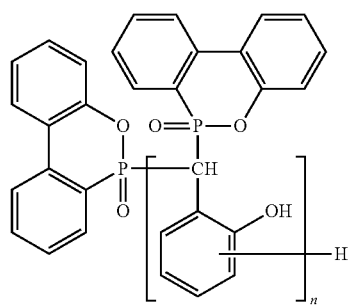

Figure 5:
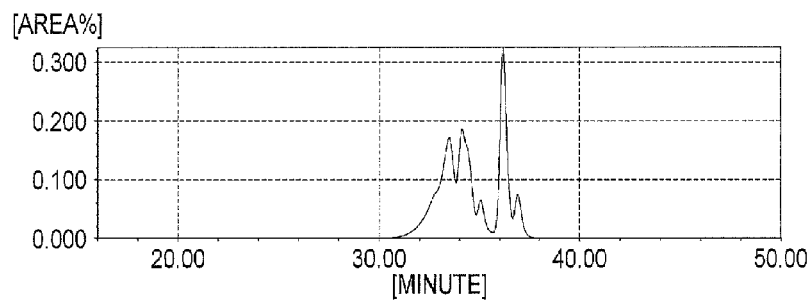
FIG. 5 shows a GPC chart of a phosphorus-containing oligomer (A-3) obtained in Example 3.

The obtained phosphorus-containing oligomer had a softening point of 150° C. (B&R method), a melt viscosity (measurement method: ICI viscometer method, measurement temperature: 180° C.) of 105 dPa·s, a hydroxyl equivalent of 363.2 g/eq, and a phosphorus content of 9.9 mass %. The content of a component whose n=1 was 33.8%, the content of a component whose n=2 was 31.2%, and the content of components whose n=3 or more was 35.0% (the content of components whose n=2 or more was 66.2%). FIG. 5 shows a GPC chart of the obtained phenolic resin.

Example 4

Synthesis of Phenolic Resin (A-4)

A flask equipped with a thermometer, a cooling tube, a fractional distillation column, a nitrogen-gas inlet tube, and a stirrer was charged with 122 g (1.0 mol) of o-hydroxybenzaldehyde, 129.6 g (0.6 mol) of HCA, and 5.54 g (0.047 mol) of oxalic acid. The mixture was heated to 120° C. to allow the reaction to proceed for two hours. Subsequently, 129.6 g (0.6 mol) of HCA was added to the flask, and the mixture was heated to 180° C. to allow the reaction to proceed for one hour. Furthermore, 172.8 g (0.8 mol) of HCA was added to the flask to allow the reaction to proceed at 180° C. for two hours. Water was then removed under heating and reduced pressure to obtain 504 g of a phenolic resin (A-4) having a structural unit represented by structural formula below.

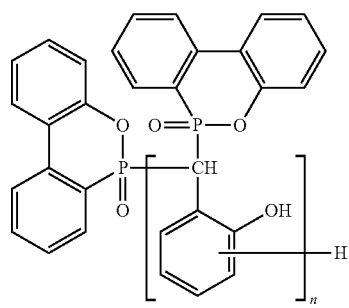

[Chem. 15]

Figure 6:
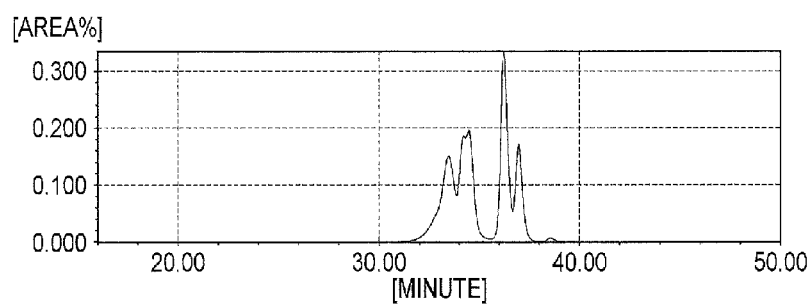
FIG. 6 shows a GPC chart of a phosphorus-containing oligomer (A-4) obtained in Example 4.

The obtained phenolic resin had a softening point of 142° C. (B&R method), a melt viscosity (measurement method: ICI viscometer method, measurement temperature: 180° C.) of 73 dPa·s, a hydroxyl equivalent of 536 g/eq, and a phosphorus content of 11.2 mass %. The content of a component whose n=1 was 43.9%, the content of a component whose n=2 was 30.1%, and the content of components whose n=3 or more was 26.0% (the content of components whose n=2 or more was 56.1%). FIG. 6 shows a GPC chart of the obtained phenolic resin.

Example 5

Synthesis of Phenolic Resin (A-5)

A flask equipped with a thermometer, a cooling tube, a fractional distillation column, a nitrogen-gas inlet tube, and a stirrer was charged with 122 g (1.0 mol) of o-hydroxybenzaldehyde, 10.8 g (0.05 mol) of HCA, and 5.54 g (0.047 mol) of oxalic acid. The mixture was heated to 120° C. to allow the reaction to proceed for two hours. Subsequently, 313.2 g (1.45 mol) of HCA was added to the flask, and the mixture was heated to 180° C. to allow the reaction to proceed for three hours. Water was then removed under heating and reduced pressure to obtain 415 g of a phenolic resin (A-5) having a structural unit represented by structural formula below.

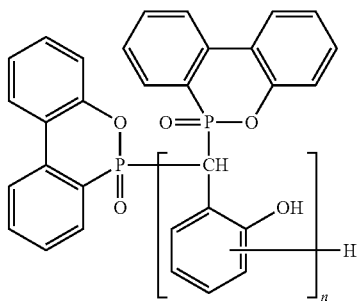

[Chem. 16]

Figure 7:
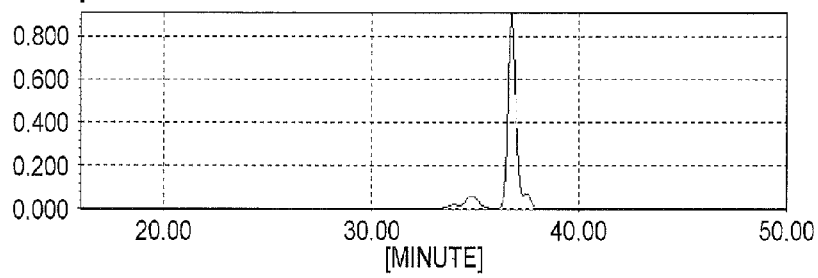
FIG. 7 shows a GPC chart of a phosphorus-containing oligomer (A-5) obtained in Example 5.

The obtained phenolic resin had a softening point of 84° C. (B&R method), a melt viscosity (measurement method: ICI viscometer method, measurement temperature: 150° C.) of 1.0 dPa·s, a hydroxyl equivalent of 420 g/eq, and a phosphorus content of 10.5%. The content of a component whose n=1 was 86.7%, the content of a component whose n=2 was 9.9%, and the content of components whose n=3 or more was 3.4% (the content of components whose n=2 or more was 13.3%). FIG. 7 shows a GPC chart of the obtained phenolic resin.

Synthetic Comparative Example 1

Synthesis of Phenolic Compound (A-6) (the Compound Disclosed in PTL 2)

A flask equipped with a thermometer, a cooling tube, a fractional distillation column, a nitrogen-gas inlet tube, and a stirrer was charged with 122 g (1.0 mol) of p-hydroxybenzaldehyde, 216 g (1.0 mol) of HCA, and 336 g of 2-propanol. The mixture was refluxed for five hours to precipitate a white solid. The white solid was then filtered, washed with 1000 mL of 2-propanol, and dried to obtain 325 g (yield: 96%) of a phenolic compound (A-6) having a structure represented by structural formula below.

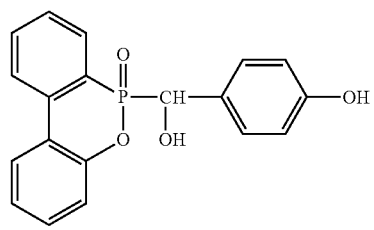

[Chem. 17]

FIG. 7 shows a GPC chart of the obtained phenolic compound.

Synthetic Comparative Example 2

Synthesis of Phenolic Resin (A-7) (the Compound Disclosed in NPL 3)

A flask equipped with a thermometer, a cooling tube, a fractional distillation column, a nitrogen-gas inlet tube, and a stirrer was charged with 236.6 g (0.7 mol) of the phenolic compound (A-6) obtained in Synthetic Comparative Example 1 and 3.08 g (0.034 mol) of oxalic acid. The mixture was heated under stirring at 180° C. for three hours. Water was then removed under heating and reduced pressure to obtain 210 g of a phenolic resin (A-7) mainly having a structural unit represented by structural formula below.

[Chem. 18]

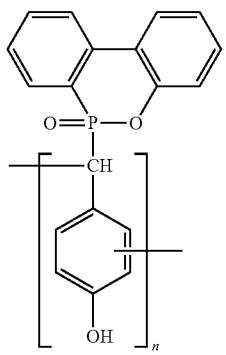

Figure 8:
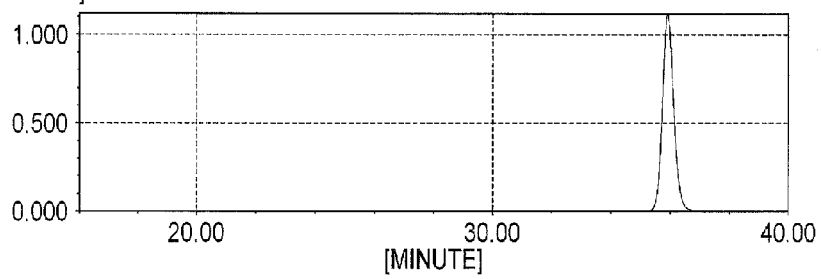
FIG. 8 shows a GPC chart of a phenolic compound (A-6) obtained in Synthetic Comparative Example 1.

The obtained phenolic resin had a softening point of 84° C. (B&R method), a melt viscosity (measurement method: ICI viscometer method, measurement temperature: 150° C.) of 1.0 dPa·s, a hydroxyl equivalent of 420 g/eq, and a phosphorus content of 9.4 mass %. The content of components whose n=2 or more was 34.0%. FIG. 8 shows a GPC chart of the obtained phenolic resin (A-7).

Synthetic Comparative Example 3

Synthesis of Phenolic Compound (A-8) (the Compound Disclosed in PTL 4)

A flask equipped with a thermometer, a cooling tube, a fractional distillation column, a nitrogen-gas inlet tube, and a stirrer was charged with 169 g (0.5 mol) of the phenolic compound (A-6) obtained in Synthetic Comparative Example 1, 47 g (0.5 mol) of phenol, and 1.25 g of p-toluene sulfonic acid. The mixture was heated to 180° C. to allow the reaction to proceed at 180° C. for eight hours. The reaction product was then filtered and dried to obtain 199 g of a phenolic compound (A-8) represented by structural formula below.

[Chem. 19]

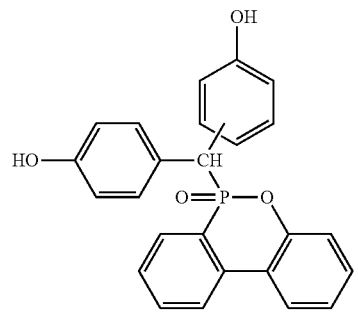

Figure 9:
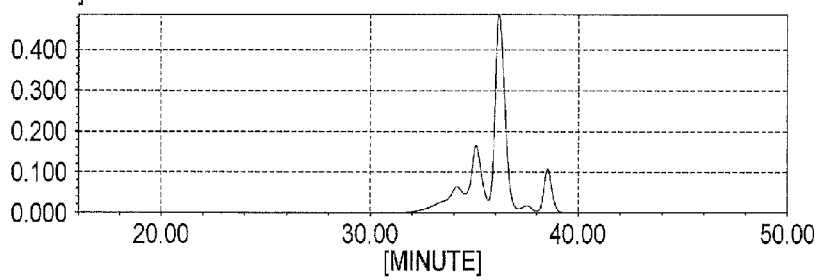
FIG. 9 shows a GPC chart of a phenolic resin (A-7) obtained in Synthetic Comparative Example 2.
Figure 10:
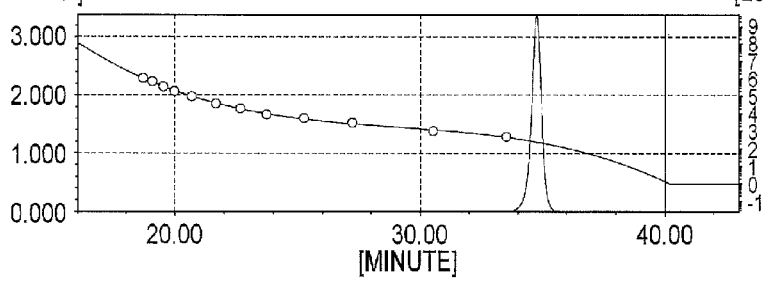
FIG. 10 shows a GPC chart of a phenolic compound (A-8) obtained in Synthetic Comparative Example 3.

The melting point of the obtained phenolic compound (A-7) was 286° C. FIG. 9 shows a GPC chart of the obtained phenolic compound (A-8).

Examples 6 to 10 and Comparative Examples 1 and 2

Test for Solubility in Solvent

Each of the phosphorus-containing oligomers (A-1) to (A-5), the phenolic resin (A-7), and the phenolic compound (A-8) was inserted into a screw-capped sample bottle in an amount of 50 g, and then each of organic solvents was added thereto in such an amount that the predetermined concentrations shown in Table 1 below were achieved. After the mixture was stirred with a shaker at room temperature, the state of the solvent in the bottle was confirmed through visual inspection. Herein, a uniformly transparent state was defined as a state of "dissolved", and a state in which a solid component was precipitated or deposited was defined as a state of "not dissolved".

TABLE 1

| Solvent | Concentration | Ex. 6 A-1 | Ex. 7 A-2 | Ex. 8 A-3 | Ex. 9 A-4 | Ex. 10 A-5 | C. E. 1 A-7 | C. E. 2 A-8 |
|---|---|---|---|---|---|---|---|---|
| Methyl ethyl ketone | 50 mass % | not dissolved | not dissolved | not dissolved | not dissolved | not dissolved | not dissolved | not dissolved |
| | 60 mass % | dissolved | dissolved | dissolved | dissolved | dissolved | not dissolved | not dissolved |
| | 70 mass % | dissolved | dissolved | dissolved | dissolved | dissolved | not dissolved | not dissolved |
| 1-methoxy-2-propanol | 50 mass % | dissolved | dissolved | dissolved | dissolved | dissolved | not dissolved | not dissolved |
| | 60 mass % | dissolved | dissolved | dissolved | dissolved | dissolved | not dissolved | not dissolved |
| | 70 mass % | dissolved | dissolved | dissolved | dissolved | dissolved | not dissolved | not dissolved |

Ex.: Example
C.E.: Comparative Example
(The abbreviations "A-1" to "A-8" in Table 1 denote the corresponding phosphorus-containing oligomers, phenolic resin, and phenolic compound.)

Examples 11 and 12 and Comparative Examples 3 to 6

Epoxy resin compositions were prepared in accordance with formulations shown in Table 2 by a method described below and then cured under the conditions below to experimentally produce multilayer plates. The multilayer plates were subjected to various evaluations. Table 2 shows the results.

[Preparation of Epoxy Resin Composition]

Epoxy resins, curing agents, and other components were mixed in accordance with the formulations shown in Table 2, and then compositions were prepared so as to finally have a non-volatile content (N.V.) of 58 mass %.

[Conditions for Producing Multilayer Plate]

Base: 100 μm; glass cloth "#2116" manufactured by Nitto Boseki Co., Ltd.
Number of plies: 6
Conditions for forming prepreg: 160° C./2 min
Copper foil: 18 μm; JTC foil manufactured by Nippon Mining & Metals Co., Ltd.
Curing conditions: 200° C., 40 kg/cm², 1.5 hours
Thickness of formed plate: 0.8 mm

[Physical Property Test Conditions]

Glass transition temperature: measured by a TMA method (compressive stress method) after an etching treatment was performed to remove a copper foil. Temperature increase rate: 10° C./min
Combustion test: the test method was in conformity with a UL-94 vertical test.
Thermal delamination test (T288 test): evaluation for thermal delamination resistance (with copper foil) at 288° C. was performed in conformity with IPC TM650.

[Chem. 5]

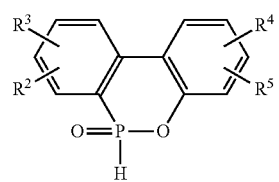

(a1-1)

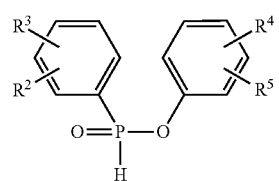

(a1-2)

(in the formula, $R^2$, $R^3$, $R^4$, and $R^5$ each independently represent a hydrogen atom, an alkyl group having 1 to 4 carbon atoms, a phenyl group, or an aralkyl group)

TABLE 2

|  |  | Example | | Comparative Example | | | |
|---|---|---|---|---|---|---|---|
|  |  | 11 | 12 | 3 | 4 | 5 | 6 |
| Epoxy resin | N-690 | 53 | 54 | 67 | 34 | 40 |  |
|  | FX-289BEK75 |  |  |  |  |  | 76 |
| Curing agent | A-1 | 27 | 27 |  |  |  |  |
|  | A-2 |  |  |  |  |  |  |
|  | A-7 |  |  |  | 66 |  |  |
|  | A-8 |  |  |  |  | 60 |  |
|  | TD-2090 | 20 | 19 | 33 |  |  | 24 |
| Curing accelerator | 2E4MZ (weight %) | 0.1 | 0.1 | 0.1 | 0.1 | 0.1 | 0.1 |
| Organic solvent | MEK | 72.4 | 72.4 | 72.4 | 72.4 | 72.4 | 72.4 |
| Glass transition temperature (TMA) (° C.) |  | 150 | 146 | 183 | Not evaluated due to crystal precipitation | Not evaluated due to crystal precipitation | 129 |
| Thermal delamination test (T288 test) |  | >120 | >120 | >120 |  |  | 0 |
| Flame retardancy | Total combustion time (second) | 28 | 32 | — |  |  | 45 |
|  | Combustion test class | V-0 | V-0 | Combustion |  |  | V-0 |

The abbreviations in Table 2 are as follows.
N-690: cresol novolac epoxy resin ("EPICLON N-690", epoxy equivalent: 215 g/eq) manufactured by DIC Corporation
FX-289BEK75: phosphorus-modified epoxy resin ("FX-289BEK75", manufactured by Tohto Kasei Co., Ltd.: epoxy resin obtained through a reaction between a cresol novolac epoxy resin and 9,10-dihydro-9-oxa-10-phosphaphenanthrene-10-oxide, epoxy equivalent: 330 g/eq, and phosphorus content: 3.0 mass %)
A-1: phosphorus-containing oligomer (A-1) obtained in Example 1
A-2: phosphorus-containing oligamer (A-2) obtained in Example 2
A-7: phenolic resin (A-7) obtained in Synthetic Comparative Example 2
A-8: phenolic compound (A-8) obtained in Synthetic Comparative Example 3
TD-2090: phenolic novolac phenolic resin ("TD-2090", manufactued by DIC Corportation, hydroxyl equivalent: 105 g/eq)
2E4MZ: 2-ethyl-4-methylimidazole

The invention claimed is:

1. A method for producing a phosphorus-containing oligomer, the method comprising mixing a compound (a1) represented by structural formula (a1-1) or (a1-2) below and a compound (a2) represented by structural formula (a2) below with each other at a molar ratio of [compound (a1)/compound (a2)]=0.01/1.0 to 0.99/1.0; causing a reaction to proceed at 80° C. to 180° C. in the presence of an acid catalyst; then adding the compound (a1) so that the total amount on a molar basis is 1.01 to 3.0 times the amount of the compound (a2) charged; and causing a reaction to proceed at 120° C. to 200° C.,

[Chem. 6]

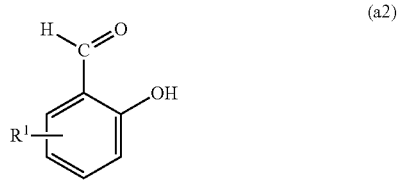

(a2)

(in the formula, $R^1$ represents a hydrogen atom, an alkyl group having 1 to 4 carbon atoms, an alkoxy group having 1 to 4 carbon atoms, or a phenyl group).

* * * * *